(12) United States Patent
Satherley et al.

(10) Patent No.: US 6,200,264 B1
(45) Date of Patent: Mar. 13, 2001

(54) AMBULATORY RECORDER HAVING WIRELESS DATA TRANSFER WITH A MULTI-PLANE LENS

(75) Inventors: Richard J. Satherley, Felbridge (GB); Malcolm G. S. Williams, Stockholm (SE)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/129,916

(22) Filed: Aug. 6, 1998

(51) Int. Cl.$^7$ ........................................ A61B 5/00
(52) U.S. Cl. ........................ 600/300; 600/301; 128/903
(58) Field of Search .................... 600/300, 301, 600/345–356; 128/903, 904

(56) References Cited

U.S. PATENT DOCUMENTS

| | | | |
|---|---|---|---|
| D. 396,037 | 7/1998 | Cappa et al. | D14/114.5 |
| 3,898,984 | 8/1975 | Mandel et al. | 128/2.1 A |
| 3,941,137 | 3/1976 | Vredenbregt et al. | 128/423 R |
| 4,003,379 | 1/1977 | Ellinwood, Jr. | 128/260 |
| 4,082,084 | 4/1978 | Lipscher | 128/2 D |
| 4,129,125 | 12/1978 | Lester et al. | 128/2.05 R |
| 4,183,354 | 1/1980 | Sibley et al. | 128/711 |
| 4,198,963 | 4/1980 | Barkalow et al. | 128/53 |
| 4,333,475 | 6/1982 | Moreno et al. | 128/711 |
| 4,353,375 | 10/1982 | Colburn et al. | 128/782 |
| 4,365,636 | 12/1982 | Barker | 128/716 |
| 4,370,983 | 2/1983 | Lichtenstein | 128/630 |
| 4,464,172 | 8/1984 | Lichtenstein | 604/65 |
| 4,503,859 | 3/1985 | Petty et al. | 128/635 |
| 4,529,401 | 7/1985 | Leslie et al. | 604/131 |
| 4,531,527 | 7/1985 | Reinhold, Jr. et al. | 128/696 |
| 4,592,018 | 5/1986 | Weigman | 365/63 |
| 4,628,928 | 12/1986 | Lowell | 128/303 R |
| 4,632,119 | 12/1986 | Reichstein | 128/632 |
| 4,667,682 | 5/1987 | Ihlenfeld, III | 128/711 |
| 4,684,367 | 8/1987 | Schaffer et al. | 604/140 |
| 4,715,385 | 12/1987 | Cudahy et al. | 128/710 |
| 4,748,562 | 5/1988 | Miller et la. | 364/415 |
| 4,771,772 | 9/1988 | DeWitt | 128/303 R |
| 4,774,956 | 10/1988 | Kruse et al. | 128/635 |
| 4,794,934 | 1/1989 | Motoyama et al. | 128/734 |
| 4,895,161 | 1/1990 | Cudahy et al. | 128/710 |
| 4,900,305 | 2/1990 | Smith et al. | 604/65 |
| 4,917,092 | 4/1990 | Todd et al. | 128/421 |
| 4,974,599 | 12/1990 | Suzuki | 128/696 |
| 5,002,062 | 3/1991 | Suzuki | 128/696 |
| 5,007,427 | 4/1991 | Suzuki et al. | 128/659 |
| 5,010,888 | 4/1991 | Jadvar et al. | 128/696 |
| 5,012,411 | 4/1991 | Policastro et al. | 364/413.06 |
| 5,016,636 | 5/1991 | Kulakowski | 128/644 |
| 5,042,481 | 8/1991 | Suziki et al. | 128/639 |
| 5,072,458 | 12/1991 | Suzuki | 2/102 |
| 5,086,778 | 2/1992 | Mueller et al. | 128/696 |
| 5,107,835 | 4/1992 | Thomas | 128/419 R |
| 5,111,396 | 5/1992 | Mills et al. | 364/413.06 |
| 5,111,818 | 5/1992 | Suzuki et al. | 128/644 |

(List continued on next page.)

FOREIGN PATENT DOCUMENTS

| | | | |
|---|---|---|---|
| 0 356 603 | 9/1988 | (SE) | A61B/5/04 |

*Primary Examiner*—Robert Nasser
(74) *Attorney, Agent, or Firm*—Thomas F. Woods; Michael J. Jaro; Harold Patton

(57) ABSTRACT

An ambulatory data recorder with enhanced infrared data transfer. In particular, the device features an infrared transmitter port having a multi-plane lens. The port, lens and recorder enclosure work together to permit a reliable infrared data link to be established between the recorder and a line voltage device even while the recorder is in a variety of positions. That is, the infrared data link may be established when the device is worn, of when the device is placed on a table in a variety of positions.

11 Claims, 6 Drawing Sheets

U.S. PATENT DOCUMENTS

| | | | |
|---|---|---|---|
| 5,113,869 | 5/1992 | Nappholz et al. | 128/696 |
| 5,117,827 | 6/1992 | Stuebe et al. | 128/635 |
| 5,131,816 | 7/1992 | Brown et al. | 417/2 |
| 5,158,083 | 10/1992 | Sacristan et al. | 128/635 |
| 5,188,104 | 2/1993 | Wernicke et al. | 128/419 R |
| 5,213,568 | 5/1993 | Lattin et al. | 604/20 |
| 5,222,503 | 6/1993 | Ives et al. | 128/731 |
| 5,224,485 | 7/1993 | Powers et al. | 128/696 |
| 5,226,431 | 7/1993 | Bible et al. | 128/904 |
| 5,228,450 | 7/1993 | Sellers | 128/711 |
| 5,238,001 | 8/1993 | Gallant et al. | 128/700 |
| 5,261,401 | 11/1993 | Baker et al. | 607/9 |
| 5,263,491 | 11/1993 | Thornton | 128/774 |
| 5,273,033 | 12/1993 | Hoffman | 607/46 |
| 5,292,344 | 3/1994 | Douglas | 607/40 |
| 5,305,202 | 4/1994 | Gallant et al. | 364/413.06 |
| 5,305,761 | 4/1994 | Byrne et al. | 128/697 |
| 5,307,263 | 4/1994 | Brown | 364/413.09 |
| 5,309,920 | 5/1994 | Gallant et al. | 128/710 |
| 5,338,157 | 8/1994 | Blomquist | 417/2 |
| 5,341,291 | 8/1994 | Roizen et al. | 364/413.02 |
| 5,343,870 | 9/1994 | Gallant et al. | 128/711 |
| 5,355,892 | 10/1994 | Saltzstein | 128/710 |
| 5,368,562 | 11/1994 | Blomquist et al. | 604/65 |
| 5,381,351 | 1/1995 | Kwong et al. | 364/571.04 |
| 5,388,587 | 2/1995 | Knutsson et al. | 128/741 |
| 5,411,022 | 5/1995 | McCue et al. | 128/632 |
| 5,429,602 | 7/1995 | Hauser | 604/65 |
| 5,431,634 | 7/1995 | Brown | 604/513 |
| 5,432,698 | 7/1995 | Fujita | 364/413.02 |
| 5,438,985 | 8/1995 | Essen-Moller | 128/633 |
| 5,479,019 | 12/1995 | Gross | 250/345 |
| 5,479,935 | 1/1996 | Essen-Moller | 128/734 |
| 5,507,904 | 4/1996 | Fisher et al. | 156/252 |
| 5,526,809 | 6/1996 | Fiddian-Green | 128/632 |
| 5,545,183 | 8/1996 | Altman | 607/5 |
| 5,607,460 | 3/1997 | Kroll | 607/30 |
| 5,645,068 | 7/1997 | Mezack et al. | 128/670 |
| 5,657,759 | 8/1997 | Essen-Moller | 128/654 |
| 5,701,894 | 12/1997 | Cherry et al. | 128/630 |
| 5,704,368 | 1/1998 | Asano et al. | 128/733 |
| 5,704,890 | 1/1998 | Bliss et al. | 600/1 |
| 5,749,907 | 5/1998 | Mann | 607/27 |
| 5,759,199 * | 6/1998 | Snell et al. | 128/903 |
| 5,833,625 * | 11/1998 | Essen-Moller | 600/547 |
| 5,848,965 * | 12/1998 | Essen-Moller | 600/350 |

* cited by examiner

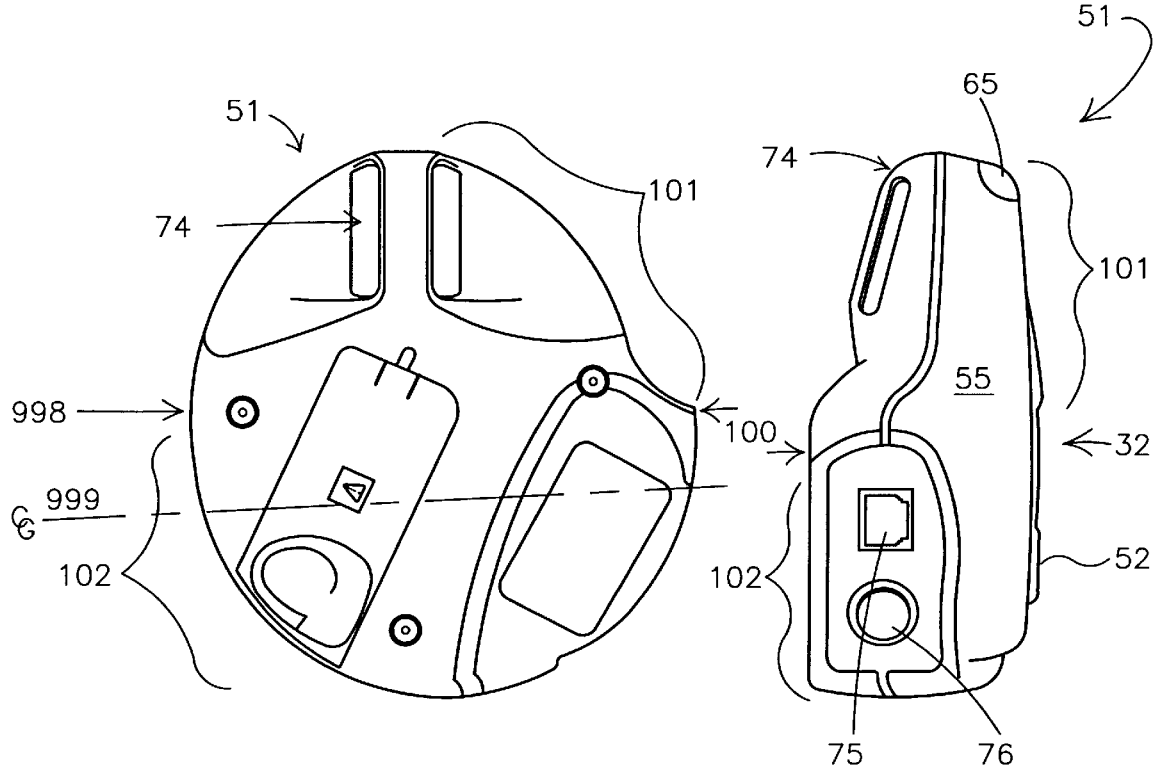
FIG. 5  FIG. 6

US 6,200,264 B1

AMBULATORY RECORDER HAVING WIRELESS DATA TRANSFER WITH A MULTI-PLANE LENS

FIELD OF THE INVENTION

The present invention relates to an ambulatory data recorder, and in particular to such a device having enhanced infrared data transfer. The device features an infrared transmitter port having a multi-plane lens; the port, lens and recorder enclosure working together to permit a reliable infrared data link to be established between the recorder and a line voltage device even while the recorder is in a variety of positions.

Ambulatory recording and recorders are widely used. Such devices include the Digitrapper Mk III™ ambulatory recorder (shown in FIGS. A and B) from Synectics Medical AB, the GastroScan II™ from Medical Instruments Corporation, and the SuperLogger™ from Sandhill Scientific. These types of devices make it possible for patients to remain at home, or at the least be ambulant in a hospital setting while physiological data is recorded. Typically the devices comprise a lightweight recorder in which the desired physiological data signals are temporarily stored and later downloaded for future analysis.

Many types of physiological data may be recorded, including ECG (Electrocardiogram) data, EEG data (Electroencephalogram) and pH or pressure data (Motility) in the gastrointestinal tract. Preferably such a recorder should be able to record among a programmable number of channels at a variety of programmable frequencies.

Ambulatory devices record data for future transfer to non ambulatory devices. In the past data was typically transmitted over a wire, such as a cable. One problem with such transfer is patient safety. If the recorder couples to a device drawing line voltage, then the recorder must be isolated to ensure patient safety. Isolation, of course, is expensive to provide and adds greater device complexity.

Thus there is a need to provide data transfer between an ambulatory recorder and a device drawing line voltage which avoids the expense and complexity of device isolation.

Other methods of transferring data may be used, such as infrared. To date these methods and in particular infrared, however, have not been satisfactory. Infrared data communications, however, have been difficult to implement in an ambulatory medical device due to the many and various ways such devices are used. That is, ambulatory devices may need to have data transferred while being worn by the patient, as well as when simply standing alone. During each of these circumstances, however, the device may be in many different positions, including vertical or horizontal or any combination thereof.

SUMMARY OF THE INVENTION

An ambulatory data recorder with enhanced infrared data transfer is described. In particular, the device features an infrared transmitter port having a multi-plane lens. The port, lens and recorder enclosure work together to permit a reliable infrared data link to be established between the recorder and a line voltage device even while the recorder is in a variety of positions. That is, the infrared data link may be established when the device is worn, or when the device is placed on a table in a variety of positions.

BRIEF DESCRIPTION OF THE DRAWINGS

FIG. 5 is a back view of the recorder.

FIG. 6 is a side view of recorder 51.

DETAILED DESCRIPTION OF THE DRAWINGS

Figure 1A:
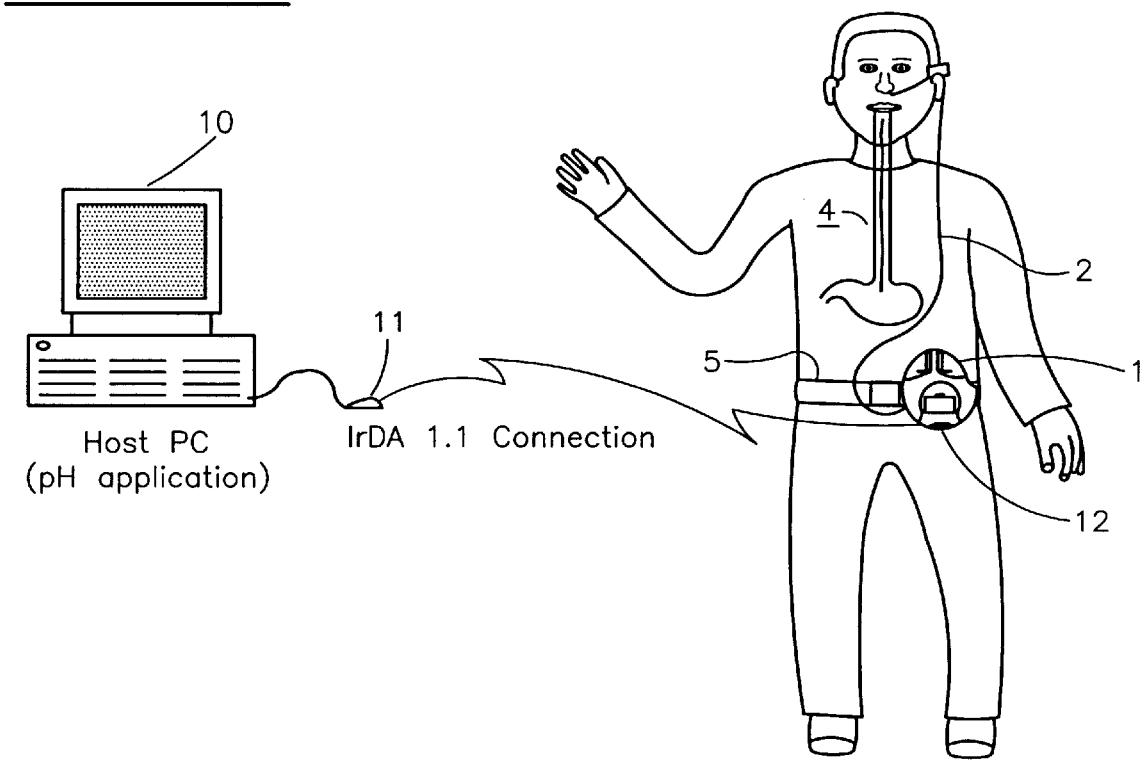
FIG. 1A depicts an ambulatory recorder of the present invention.

FIG. 1A depicts an ambulatory recorder of the present invention. As seen, ambulatory recorder 1 of the present invention may be carried by a patient. In the preferred embodiment, recorder 21 may be either carried through a mounting in the back of the recorder enclosure which fastens to patient's belt 5, or the same mounting may be coupled to be carried using a shoulder harness (not shown). Recorder 1 is coupled to patient 4 through one or more sensing catheters 2. Sensing catheters may be positioned in any area of the patient's body from which data is to be sensed, including the esophagus, as depicted in FIG. 1A. It should be noted the ambulatory recorder of the present invention may be used to collect many or various types of data including gastrointestinal (including pH and pressure) data, neurological data, as well as neuromuscular, EEG data or EMG data.

Among the various sensing catheters which may be coupled to the device are manometry catheters and pH testing catheters, including the Synectics Medical AB, Stockholm, Sweden Model G 91-9 series of Multi use pH catheters; Synectics Medical AB Model G 91-2 series of Multi use pH catheters with perfusion port; or the Zinectics Inc., Salt Lake City, Utah disposable 24 pH catheter Model series G91-6 or G 91-7. While a single catheter 2 is shown depicted in this figure, recorder 1 further permits two separate sensors to be coupled to the device, as seen in FIG. 1B.

As further seen in this figure, the recorder may also communicate with a host PC 10 via an infra red data link facility through an IrDA connection 11, such as for example, a JETEYE ESI-57680 available form Extended Systems, Inc., Boise, Id., which communicates with the recorder using the infra Red Data Association 1.1 Connection Protocol. As seen, infra red data connection makes a link to infra red port 12 on recorder 1.

Figure 1B:
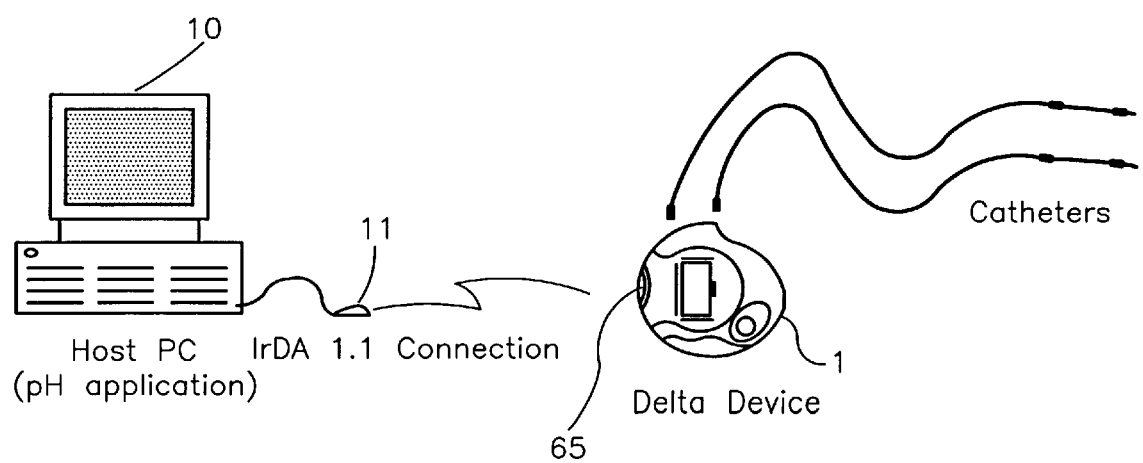
FIG. 1B illustrates a further manner in which recorder 1 may also have an infra red data communication link established with a host PC.

FIG. 1B illustrates a further manner in which recorder 1 may also have an infra red data communication link established made with a host PC. In particular, infra red data communication may be further established when the recorder is not worn by the patient. As discussed in more detail below, one of the advantages of the present invention is that the infra red data components and recorder case permit such a link to be made when the device is worn as shown in FIG. 1A, as well as when the device is removed from the patient and positioned in proximity to mouse 11.

Figure 2:
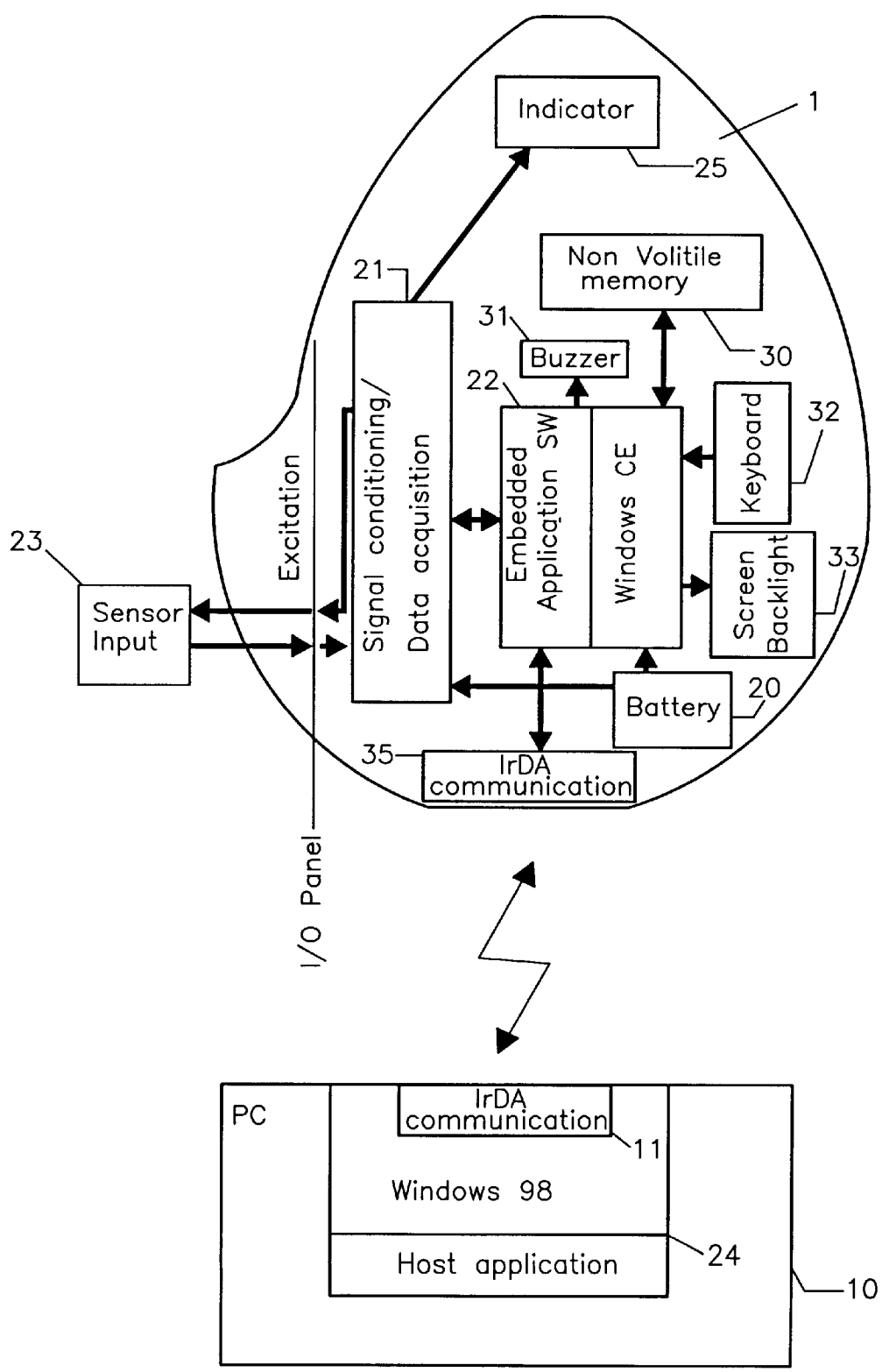
FIG. 2 is a block diagram of the data recording system shown in FIG. 1B.

FIG. 2 is a block diagram of the data recording system shown in FIG. 1B. As seen, recorder 1 features a battery 20 which is coupled to the signal conditioning/data acquisition block that is driven by a real time processor 21. The battery is coupled as well as to a non-real time processor 22 that runs the application. In the preferred embodiment battery 20 is provided by a pair of "AA"-type batteries. As disclosed in more detail below, real time processor 21 is a low power processor which is used to sample data received from sensor input 23 by a sensor attached thereto (not shown in FIG. 2.).

Sampling is achieved through the signal conditioning providing an excitation to the sensor coupled to sensor input 23. Such excitation voltage is often used to power and, thus, permit sensing to occur in a variety of different types of sensors, including pressure sensors, as is well known in the art. The sampling and sensing controls are provided by real time processor 21. Real time processor 21 also drives LED indicator 25 to show the system is running even when the screen is off.

As further seen, this processor is coupled to second non-real time processor 22. Second processor 22 is provided primarily to perform those high processing operations associated with multitasking, graphical user interface, floating point calculation, Infra Red communication and long term memory storage. In particular, the second processor is primarily provided to operate a Windows CE operating system as well as one or more embedded applications, as depicted. As further seen, this processor is coupled to audible buzzer 31 as well as keyboard controls 32, a screen 33 and non-volatile memory 30. Non-volatile memory provides a long term memory for the device such that data can be recorded and preserved even if power is lost. In the preferred embodiment, keyboard controls processes a series of four push buttons, each of which provide one or more different types of system inputs, as provided by the Windows CE™ operating system, available from Microsoft Corporation, Redmond, Wash.

As further seen in this figure, recorder 1 features an infra red port 35 to communicate with the host PC. As depicted in FIG. 1B, the infra red connection permits the recorder 1 to receive and exchange data with host PC 10. Host PC, as seen, includes both a Windows 98™ operating system available from Microsoft Corporation, Redmond, Wash., as well as one or more host applications. Host applications permit the treatment of the recorded values and help for diagnostic.

In a preferred embodiment of the present invention the real time processor 21 is a model PIC16LC67IC from Microchip Technology Inc., Chandler, Ariz.; non-real time processor 22 is a model ElanSC400IC from Advanced Micro Devices, Inc. Sunnyvale, Calif.; and non-volatile memory 30 a model Minicard AMMCL004AWP from Advanced Micro Devices, Inc. Sunnyvale, Calif.

Figure 3:
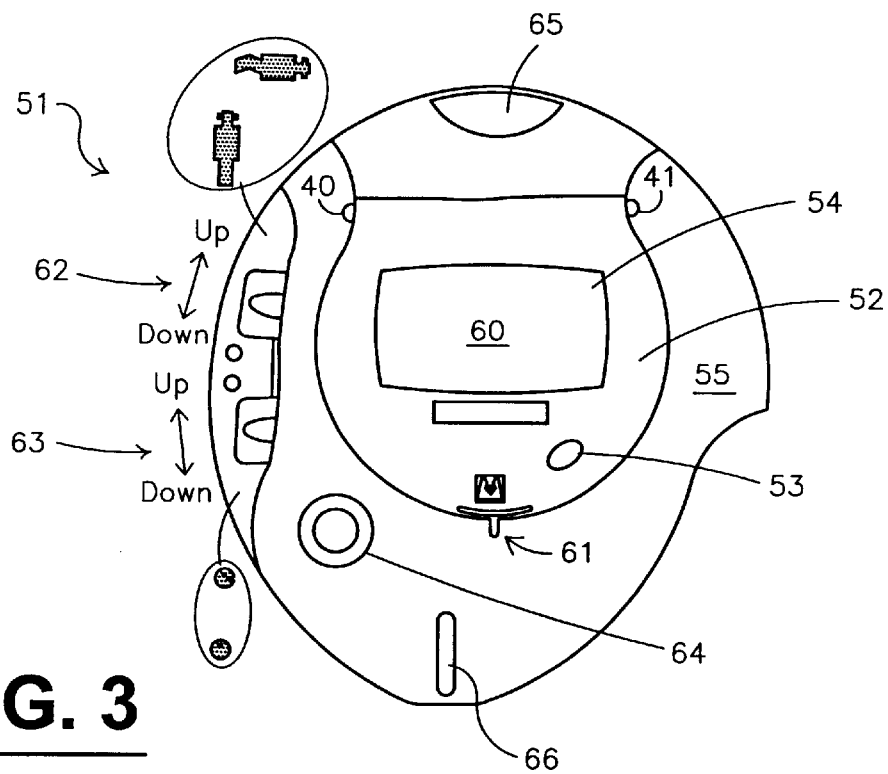
FIG. 3 is a front view of recorder according to the present invention.

FIG. 3 is a front view of recorder according to the present invention. In this view, recorder 51 has its movable front cover 52 closed. As discussed in more detail below, front cover further includes a movable push button shield 53 which allows access to one of the push button controls covered by the cover while in the down position. Shield 53, although allowing access to the push button controls, obscures any notation of the push button controls from the viewer when the cover is closed such that a very simplified control interface is presented to any user when the cover 52 is closed. Cover 52 also features transparent window 54 to permit viewing of LCD screen 60 which is integral with recorder 1 (further depicted in FIG. 2). As mentioned, cover 52 may be moved from a closed position, shown in this figure, to an open position, shown in FIG. 4. Movement is controlled by cover catch 61, described in more detail in FIG. 9.

As seen, recorder 1 also features a pair of period switches 62 and 63 which are movable in a linear fashion from a first to a second position. In the preferred embodiment, period switch 62 is a body position switch, and the up position is used to mark periods when the patient is lying down or in a supine position. The down position is used to mark periods when the patient is standing or sitting upright. Period switch 63 preferably is a meal switch and the up position is used to mark a meal period while the down position is used for periods when the patient is not eating. The device further features, an event button 64 which the patient presses to mark events. Such events may include heart palpitations or reflux. Clock button 53, period switches 62 and 63 and event button 64 are all coupled to the keyboard function 32, shown in FIG. 2.

The device further features an infra red data output port having a two plane infra red lens 65. This feature is coupled to the infra red communication block 35 depicted in FIG. 2 and permits the device to communicate, through an infra red connection, to a host PC. The device also features an operation indicator light 66 which would indicate device operation.

Figure 4:
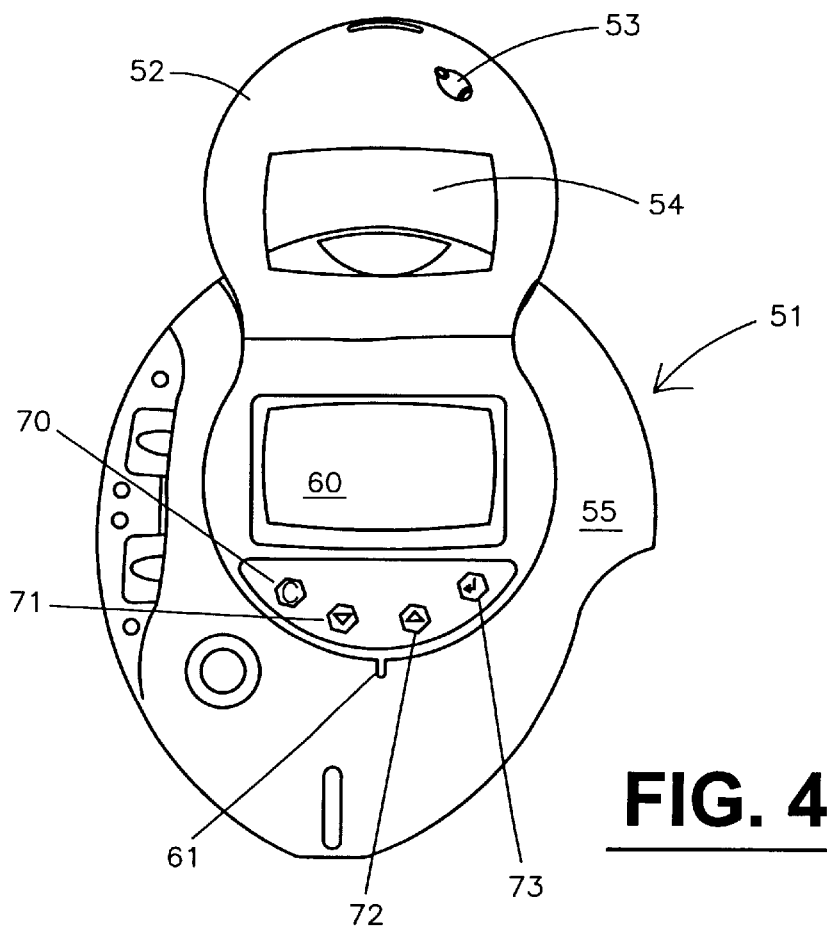
FIG. 4 is a front view of recorder 51 in which cover 52 has been raised.

FIG. 4 is a front view of recorder 51 in which cover 52 has been raised and the device is open. As seen, when open, a series of controls 70, 71, 72 and 73 are exposed. Control 70 is a push button and features, at its front face, the mark C. This control permits the user to return to the previous screen shown on display 60 without having to save any changes. Control 71 is a push button which, in the preferred embodiment, moves the selection bar shown in 60 to the next item down. Control 72 is a push button which, in the preferred embodiment, moves the selection bar to the next item up. Control 73 is, preferably, a push button which executes the current selection in the preferred embodiment.

As seen by a comparison of FIG. 3 and FIG. 4, control push button 73 may be operated regardless of whether the cover is opened or closed during the provision of movable push button 53. An important feature of this shield, however, is that it presents a different notation for the push button when the cover is closed as compared to when the cover is open. As discussed above, past ambulatory recorders have performed less than satisfactorily because too many controls were presented to the patient. While such controls are necessary to be presented to the physician so that the device may be programmed and its operating parameters set in an acceptable manner, such controls are not necessary for the patient when the device is merely recording. Thus, the movable push button shield, mounted to the movable cover, permits the device to provide an enhanced control feature set to a physician while limiting the control feature set for the patient. Cover movement is further controlled by open cover catch 61 which permits the cover to be opened only with a tool, which in the preferred embodiment is a pen tip. Although not shown in this figure, another feature important to the device operation is that of the hinge point on which the cover is mounted. In the preferred embodiment, the hinge is functionally a break-away hinge such that if excessive force (e.g. greater than eight pounds) is provided to the cover when open it will release from its hinge points without breaking such that it may thereafter be reinserted into its hinge. The breakaway feature is provided in a known manner, such as a deformable polymer cover along with removable hinges, e.g. interlocking hemispherical hinge points and recesses. The break-away hinge is provided through the engagement of a pair of oppositely disposed pins 90 and 91 (shown here as a dotted line) integral with cover 52 which engage into enclosure 55 and, thus, permit cover to be rotated from an open to a close position and vice versa. Break-away capability is provided because the pins are of limited dimension such that they can, upon sufficient force, be moved out of the corresponding recesses and enclosure and, thus, permit cover 52 to break-away or release without further damage.

FIG. 5 is a back view of the recorder. As seen, recorder 51 features a belt loop 74 which may be used to mount the recorder to a patient using either the patient's belt or the shoulder strap. As also seen in this view, the device further features a unique weight distribution, particularly involving the device's batteries. As seen, center of gravity 999 of the recorder taken within the major plane with the battery inserted is located below the widest portion of the recorder, generally designated as 998. This distribution of the weight below the case widest portion ensure the recorder hangs in a stable manner when worn.

FIG. 6 is a side view of recorder 51. As further seen in this view, housing 55 features a pair of sensor inputs 75 and 76. In the preferred embodiment, input 75 is for a pH catheter while input 76 is for a pressure measuring catheter. As further seen, recorder features an infra red lens 65 which permits an infrared link to a host be made using the IrD communication components shown in FIG. 2. As seen in this view, lens 65 is positioned along both an upper as well as a side surface of the recorder enclosure. This two sided or multi plane lens thereby permits a large degree of exposure to the internal IrD components inside the enclosure and thus permits an IrD link to be made with the recorder in a variety of positions relative to the IrDA communication device 11 (referring to FIGS. 1A and 1B). Lens 65 may be made of an known standard lens material. In the preferred embodiment lens 65 is made of polycarbonate and the enclosure itself, including the cover, is fashioned from the polymer Crastin™ XMB 850 FR available from E. I. Du Pont De Nemours And Company, Wilmington, Del. The lens, however, should be formed so as to reach across both the upper side as well as front side of the recorder (referring once again to FIG. 6).

Figure 7:
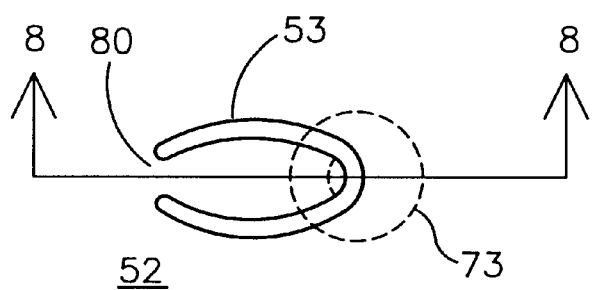
FIG. 7 is a detailed view of the movable push button shield.

FIG. 7 is a detailed view of the movable push button shield. As seen, movable push button shield 53 is designed to be positioned proximate the push button control 73, shown here as a dotted line. Shield 53 is provided by cutting away the elongated section of cover such that a cantilevered strip remains. As seen, in the preferred embodiment, the cantilever strip is somewhat oval in shape, although many or various types of shapes may also be used. The partial cutting away leaves the cantilever strip as a flexible hinge portion generally depicted here as 80 and permits the cantilever strip to open and thus be used to actuate push button.

Figure 8:
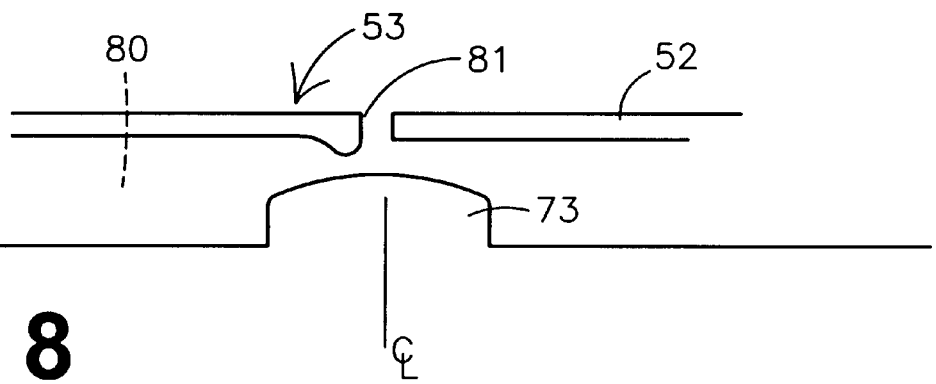
FIG. 8 is a sectional view of FIG. 7.

FIG. 8 is a sectional view of FIG. 7. As seen, the cantilever section, and the hinge which provides flexibility, are disposed generally off-center from push button 73 such that the distal end of cantilever section 81 is shown in alignment with the center line of push button 73. The distal end further features a pronounced footing to further assist in the engagement of shield 53 with push button and thus facilitate push button operation.

Figure 9:
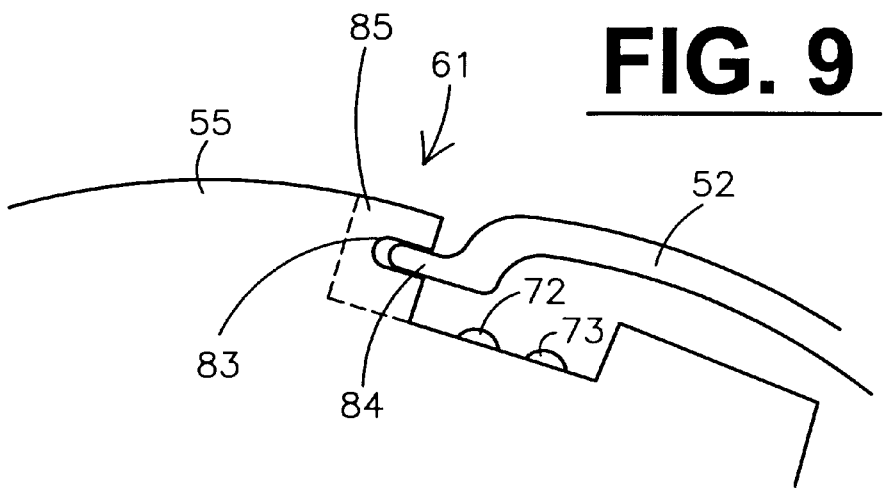
FIG. 9 is a detailed sectional view of catch.
Figure 10:
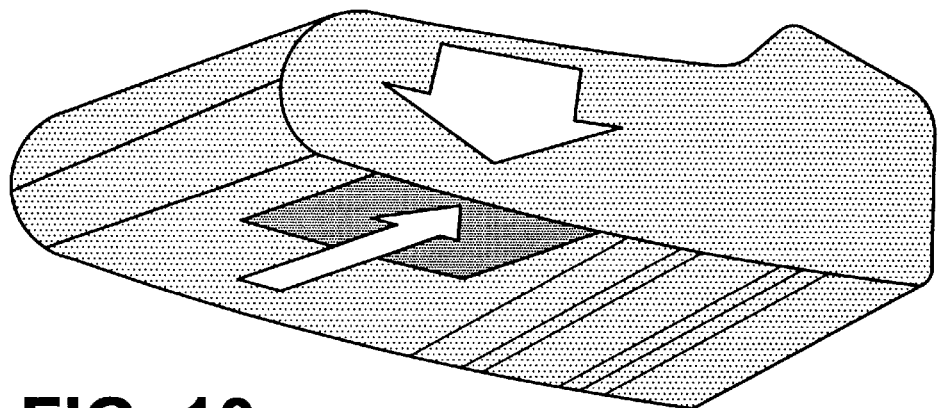
FIGS. 10 and 11 depict the prior art Digitrapper Mk III™ ambulatory recorder from Synectics Medical AB. The Figures are not necessarily to scale.
Figure 11:
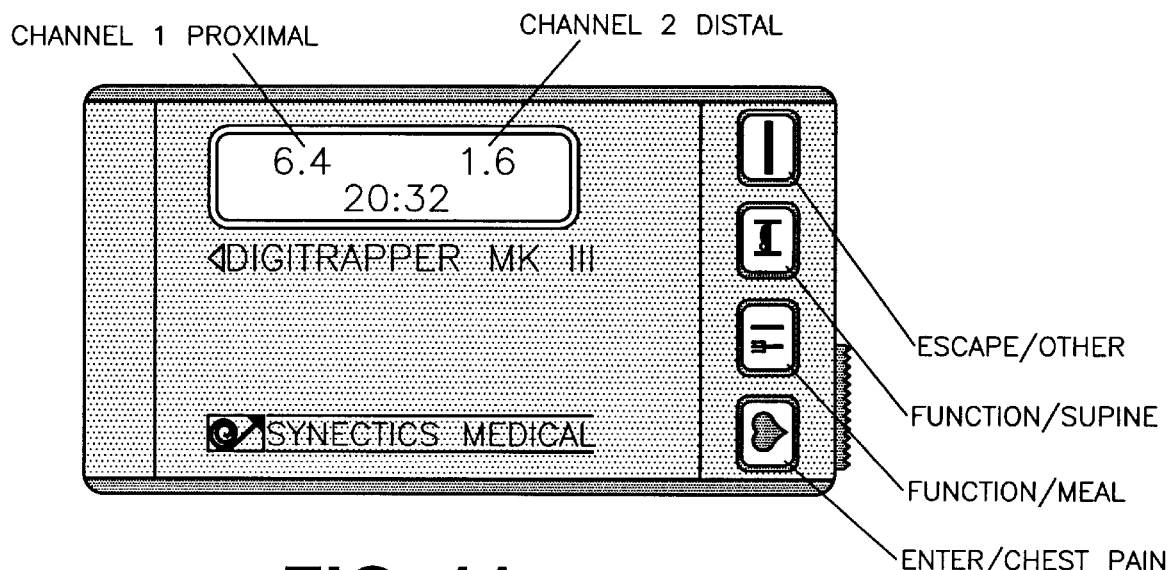

FIG. 9 is a detailed sectional view of catch 61. As discussed above, the cover may be only opened or closed through the release of catch 61. As seen, catch 61 features a recess 83 which co-operates with a finger 84 provided on cover 52. Because the cover is flexible, however, it may be deformed enough to disengage finger from recess.

As further seen in this FIG. 9 and also in FIG. 3, trench 85 is provided in housing 55 to permit the engagement and, thus, removal of tongue from recess.

Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An ambulatory medical data recorders comprising:
   an enclosure, the enclosure having a first major exterior upper surface and a second major exterior side surface, the first and second surfaces being substantially oriented along non-parallel first and second plants, respectively;
   a processor for sampling sensed physiologic data, the processor being disposed within the enclosure;
   an infrared data transmitter coupled to the processor, the infrared transmitter being positioned within the enclosure;
   a sensor for sensing physiologic data, the sensor being coupled to the processor such that data sensed by the sensor may be transferred to the processor; and
   an infrared communication lens, the lens being secured to the enclosure and defining an infrared pathway from the infrared data transmitter to the exterior surfaces of the enclosure, the lens being disposed along and contiguous with both the first major surface and the second major surface such that the lens straddles both the first major surface and the second major surface to thereby permit the recorder to establish a reliable infrared communication link with an external device when the recorder is placed in any one of a plurality of physical orientations respecting the external device.

2. The ambulatory medical data recorder of claim 1, wherein the processor further comprises a memory for storing the sensed data.

3. The ambulatory medical data recorder of claim 1, wherein the first major surface is substantially orthogonal to the second major surface.

4. The ambulatory medical data recorder of claim 3, further comprising push buttons controls to control the processor.

5. The ambulatory medical data recorder of claim 3, wherein the enclosure further comprises means for mounting the recorder to a patient.

6. The ambulatory medical data recorder of claim 1, wherein the sensor is incorporated into a catheter.

7. An ambulatory medical data recorder, comprising:
   means for providing a connection to a sensor for sensing at least one physiologic signal;
   means for recording the at least one signal, the signal recording means being configured to record the at least one signal and further being coupled to the catheter connection means;
   an infrared data transmitter coupled to the signal recording means;
   an enclosure having the signal recording means, the sensor connection means and the infrared data transmitter disposed therein or attached thereto the enclosure further comprising a first major exterior upper surface and a second major exterior side surface, the first and second surfaces being substantially oriented along non-parallel first and second planes, respectively;

an infrared communication lens, the lens being secured to the enclosure and defining an infrared pathway from the infrared data transmitter to the exterior surfaces of the enclosure, the lens being positioned along and contiguous with both the first major surface and the second major surface such that the lens straddles both the first major surface and the second major surface to thereby permit the recorder to establish a reliable infrared communication link with an external device when the recorder is placed in any one of a plurality of physical orientations respecting the external device.

8. The ambulatory medical data recorder of claim 7, wherein the signal recording means and the infrared data transmitter are powered by a battery.

9. The ambulatory medical data recorder of claim 7, wherein the sensor is incorporated into a catheter.

10. The ambulatory medical data recorder of claim 7, wherein the sensor is a pH sensor.

11. The ambulatory medical data recorder of claim 10, further comprising means for mounting the enclosure to a patient.

* * * * *